United States Patent
Yamaguchi et al.

(10) Patent No.: US 9,462,972 B2
(45) Date of Patent: Oct. 11, 2016

(54) DEMENTIA DIFFERENTIATION DEVICE

(71) Applicant: The University of Tokyo, Bunkyo-ku, Tokyo (JP)

(72) Inventors: Yasuhiro Yamaguchi, Tokyo (JP); Yasuyoshi Ouchi, Tokyo (JP); Shinichiro Hibi, Tokyo (JP)

(73) Assignee: The University of Tokyo, Tokyo (JP)

( * ) Notice: Subject to any disclaimer, the term of this patent is extended or adjusted under 35 U.S.C. 154(b) by 101 days.

(21) Appl. No.: 14/415,550

(22) PCT Filed: Jul. 17, 2013

(86) PCT No.: PCT/JP2013/069340
§ 371 (c)(1),
(2) Date: May 28, 2015

(87) PCT Pub. No.: WO2014/013999
PCT Pub. Date: Jan. 23, 2014

(65) Prior Publication Data
US 2015/0257696 A1   Sep. 17, 2015

Related U.S. Application Data

(60) Provisional application No. 61/672,918, filed on Jul. 18, 2012.

(51) Int. Cl.
*A61B 5/11* (2006.01)
*A61B 5/00* (2006.01)

(52) U.S. Cl.
CPC ............ *A61B 5/4088* (2013.01); *A61B 5/11* (2013.01); *A61B 5/1123* (2013.01); *A61B 5/4818* (2013.01); *A61B 5/6828* (2013.01); *A61B 5/7246* (2013.01); *A61B 5/7275* (2013.01)

(58) Field of Classification Search
CPC .... A61B 5/4088; A61B 5/11; A61B 5/1123; A61B 5/4818; A61B 5/6828; A61B 5/7246; A61B 5/7275
See application file for complete search history.

(56) References Cited

U.S. PATENT DOCUMENTS 8,249,686 B2 *   8/2012   Libbus ................. A61B 5/0002
                                                              600/301

OTHER PUBLICATIONS

Hanyu, H., et al., "Comparative Value of Brain Perfusion SPECT and [$^{123}$I]MIBG Myocardial Scintigraphy in Distinguishing Between Dementia With Lewy Bodies and Alzheimer's Disease," European Journal of Nuclear Medicine and Molecular Imaging 33(3):248-253, Mar. 2006.

*Primary Examiner* — Catherine Voorhees
(74) *Attorney, Agent, or Firm* — Christensen O'Connor Johnson Kindness PLLC (57) ABSTRACT

A leg movement acquisition unit 1 continuously acquires leg movements of a sleeping subject. An apnea detection unit 2 detects whether or not the subject is in a state of apnea. A movement analysis unit 3 determines whether or not the detected leg movement satisfies previously determined conditions. These previously determined conditions include at least the following conditions (a) to (d): (a) The duration of leg movement is within a previously determined range; (b) intensity of leg movement is a previously determined value or greater; (c) leg movements satisfying conditions (a) and (b) continue for a previously determined number of times within a previously determined duration; and (d) the leg movement is not movement from immediately before to immediately after an apnea state that has been detected by the apnea detection unit. A coefficient calculation unit 4 calculates a coefficient based on the number of times of leg movement that satisfied the previously determined conditions. An output unit 6 outputs the coefficient or a determination result based on the coefficient.

6 Claims, 5 Drawing Sheets

DEMENTIA DIFFERENTIATION DEVICE

TECHNICAL FIELD

The present invention relates to technology for differentiating types of dementia.

BACKGROUND ART

Dementia is classified into Alzheimer's type dementia (hereafter sometimes called "AD"), and Lewy Body type dementia (hereafter sometimes called "DLB"), depending on the causes and symptoms of the dementia. Appropriate courses of treatment are selected in accordance with this classification. DLB is the second most common neurodegenerative dementia after AD, accounting for 15-25% of elderly dementia patients.

Correct diagnosis is difficult, since initial symptoms of AD and DLB are similar. In order to correctly differentiate the two, it is currently necessary to carry out Single Photon Emission Computed Tomography (so-called "SPECT") or MIBG scintigraphy (refer, for example, to non-patent publication 1 below). However, devices for implementing these procedures are extremely costly, and are difficult to install in normal hospitals.

Initial assessment for dementia classification is important for determination of course of treatment, and so it is desired to provide technology that can carry out differentiation of AD and DLB accurately with a simple and inexpensive procedure.

CITATION LIST

Non-Patent Literature

Non-Patent Publication 1: Hanyu H., Shimizu S., Hirao K., Kanetaka H., Iwamoto T., Chikamori T., et al. Comparative value of brain perfusion SPECT and [(123)I] MIBG myocardial scintigraphy in distinguishing between dementia with Lewy bodies and Alzheimer's disease. European Journal of Nuclear Medicine and Molecular Imaging 2006; 33:248-53.

SUMMARY OF THE INVENTION

Technical Problem

The present invention has been conceived in view of the above-described situation. The main object of the present invention is to provide technology that can carry out differentiation of AD and DLB accurately with a simple and inexpensive procedure.

Solution to Problem

The present invention has a configuration disclosed in any of the following aspects.

(Aspect 1)

A dementia differentiation device, comprising a leg movement acquisition unit, an apnea detection unit, a movement analysis unit a coefficient calculation unit and an output unit, wherein the leg movement acquisition unit continuously acquires leg movements of a sleeping subject, the apnea detection unit detects whether or not the subject is in a state of apnea, and the movement analysis unit determines whether or not the leg movements satisfy previously determined conditions, the previously determined conditions including at least the following conditions (a) to (d):

(a) the duration of leg movement is within a previously determined range;

(b) the intensity of leg movement is a previously determined value or greater;

(c) leg movements satisfying conditions (a) and (b) continue a previously determined number of times within a previously determined duration; and (d) the leg movement is not movement from immediately before until immediately after a state of apnea that has been detected by the apnea detection unit, and wherein the coefficient calculation unit calculates a coefficient based on the number of times of leg movement that satisfied the previously determined conditions, and the output unit outputs either the coefficient or a determination result based on the coefficient.

(Aspect 2)

The dementia differentiation device of aspect 1, further comprising a comparison unit, wherein the comparison unit determines the determination result by comparing a threshold value for determining whether or not a symptom is lewy body dementia and the coefficient that has been calculated by the coefficient calculation unit, and the output unit outputs the determination result that has been determined by the comparison unit.

(Aspect 3)

The dementia differentiation device of aspect 1 or aspect 2, wherein the coefficient based on the number of times of leg movement is an average number of times per unit duration of the leg movements that satisfied the previously determined conditions, for a sleeping subject.

(Aspect 4)

The dementia differentiation device of any one of aspects 1-3, wherein the leg movement acquisition unit acquires the leg movement by measuring myoelectric potential of a leg of the subject (Aspect 5)

An operating method for a dementia differentiation device, comprising a leg movement acquisition unit, an apnea detection unit, a movement analysis unit a coefficient calculation unit and an output unit, wherein leg movement of a sleeping subject that has been acquired by the leg movement acquisition unit, and a detection result as to whether or not the subject is in a state of apnea, that has been detected by the apnea detection unit, are used, and a step of the movement analysis section determining whether or not the leg movements satisfy previously determined conditions is provided, the previously determined conditions including at least the following conditions (a) to (d):

(a) the duration of leg movement is within a previously determined range;

(b) the intensity of leg movement is a previously determined value or greater;

(c) leg movements satisfying conditions (a) and (b) continue a previously determined number of times within a previously determined duration; and (d) the leg movement is not movement from immediately before until immediately after a state of apnea that has been detected by the apnea detection unit, and wherein the method further comprises a step of the coefficient calculation unit calculating a coefficient based on the number of times of leg movement that satisfied the previously determined conditions, and a step of the output unit outputting either the coefficient or a determination result based on the coefficient.

(Aspect 6)

A computer program, for causing operation of a dementia differentiation device, comprising a leg movement acquisition unit, an apnea detection unit, a movement analysis unit, a coefficient calculation unit and an output unit, wherein leg movement of a sleeping subject that has been acquired by the leg movement acquisition unit, and a detection result as to whether or not the subject is in a state of apnea, that has been detected by the apnea detection unit, are used, and a computer causes the movement analysis unit to execute a step of determining whether or not the leg movements satisfy previously determined conditions, the previously determined conditions including at least the following conditions (a) to (d):

(a) the duration of leg movement is within a previously determined range;

(b) the intensity of leg movement is a previously determined value or greater;

(c) leg movements satisfying conditions (a) and (b) continue a previously determined number of times within a previously determined duration; and (d) the leg movement is not movement from immediately before until immediately after a state of apnea that has been detected by the apnea detection unit, and wherein this computer program further causing a computer to execute a step of causing the coefficient calculation unit to calculate a coefficient based on the number of times of leg movement that satisfied the previously determined conditions, and a step of causing output of either the coefficient or a determination result based on the coefficient in the output unit.

This computer program may be stored in an appropriate storage medium (for example, optical storage medium such as CD-ROM or DVD disk, magnetic storage medium such as hard disk or flexible disk, or magnet-optical storage medium such as MO disk). This computer program may also be transmitted by means of communication lines such as the Internet.

(Aspect 7)

An operating method for a dementia differentiation device, wherein leg movement of a sleeping subject and a detection result as to whether or not the subject is in a state of apnea are used, and a step of the movement analysis unit of the dementia differentiation device determining whether or not the leg movements satisfy previously determined conditions is provided, the previously determined conditions including at least the following conditions (a) to (d):

(a) the duration of leg movement is within a previously determined range;

(b) the intensity of leg movement is a previously determined value or greater;

(c) leg movements satisfying conditions (a) and (b) continue a previously determined number of times within a previously determined duration; and (d) the leg movement is not movement from immediately before until immediately after a state of apnea of the subject, and wherein this method further comprises a step of the coefficient calculation unit of the dementia differentiation device calculating a coefficient based on the number of times of leg movement that satisfied the previously determined conditions, and a step of the output unit of the dementia differentiation device outputting either the coefficient or a determination result based on the coefficient.

Advantageous Effects of the Invention

The present invention provides the above configurations, to make it possible to accurately carry out differentiation of AD and DLB with a simple and inexpensive procedure.

DESCRIPTION OF THE EMBODIMENTS

Structure of the Embodiment

Figure 1:
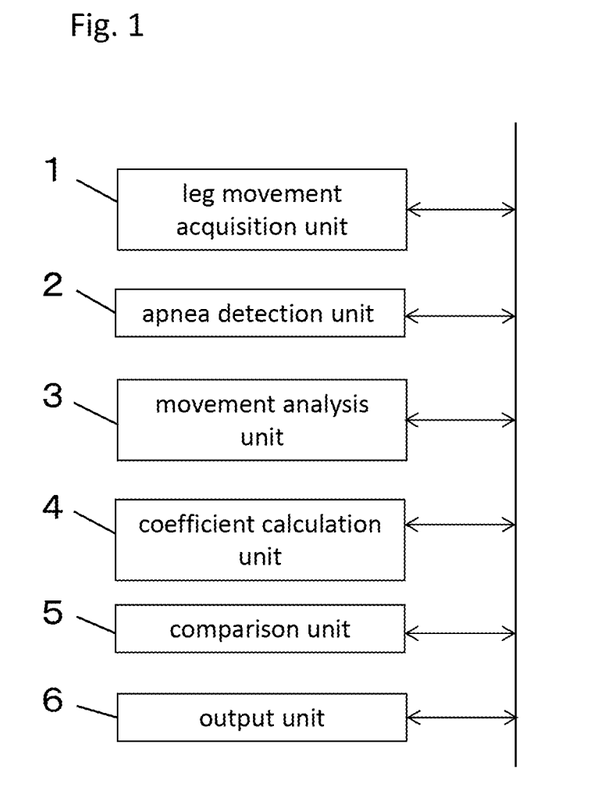
FIG. 1 is a block diagram showing the schematic structure of a dementia differentiation device of one embodiment of the present invention.

A dementia differentiation device of one embodiment of the present invention will be described in the following based on the attached drawings. The dementia differentiation device of this embodiment comprises a leg movement acquisition unit 1, an apnea detection unit 2, a movement analysis unit 3, a coefficient calculation unit 4 and an output unit 6 (refer to FIG. 1). The device of this example further comprises a comparison unit 5.

(Leg Movement Acquisition Unit)

The leg movement acquisition unit 1 continuously acquires leg movements of a sleeping subject. More specifically, the leg movement acquisition unit 1 of this embodiment acquires leg movement by measuring myoelectric potential of a subject's leg. The leg movement acquisition unit 1 of this example is provided with electrodes 11 for myoelectric potential measurement (refer to FIG. 2), and contraction of muscles of a leg L (namely leg movement) can be detected by attaching the electrodes 11 to the leg L of a subject. As the leg movement acquisition unit it is possible to use a device that acquires leg movement by detecting acceleration, instead of with myoelectric potential. However, using myoelectric potential makes it possible to detect leg movement with higher accuracy than in the case where acceleration is used.

(Apnea Detection Unit)

The apnea detection unit 2 detects whether or not the subject is in a state of apnea. Specifically, the apnea detection unit 2 can detect airflow of the nose and mouth of the subject, and can determine that there is apnea as a result of the airflow being less than a predetermined value. Alternatively, as the apnea detection unit 2, a method of detecting positional displacement of the chest region accompanying breathing using an acceleration sensor; or a method of perceiving change in body pressure of the lower side of the body accompanying breathing while sleeping using a pressure sensor, etc.

may be used.

It is possible to use already known technology as such an apnea detection unit 2, and so more detailed description is omitted.

(Movement Analysis Unit)

The movement analysis unit 3 determines whether or not the detected leg movement satisfies previously determined conditions. These previously determined conditions include at least the following conditions (a) to (d):

(a) the duration of leg movement is within a previously determined range;

(b) intensity of leg movement is a previously determined value or greater;

(c) leg movements satisfying conditions (a) and (b) continue for a previously determined number of times within a previously determined duration; and (d) the leg movement is not movement from immediately before to immediately after an apnea state that has been detected by the apnea detection unit.

Detailed operation of the movement analysis unit 3 will be described later.

(Coefficient Calculation Unit)

The coefficient calculation unit 4 calculates a coefficient based on the number of times of leg movement that satisfied the previously determined conditions. As the coefficient here, with this example, and average number of times per unit time for leg movements of a sleeping subject that have satisfied the previously determined conditions is used. More specifically, as the coefficient of this example, a so-called PLM (Periodic limb movements during sleep) index is used. A specific example of coefficient calculation will also be described later.

(Comparison Unit)

The comparison unit 5 determines a determination result for dementia differentiation by comparing a threshold value for determining whether or not there is lewy body dementia with the coefficient that has been calculated by the coefficient calculation unit 4. A specific example of determination will also be described later.

(Output Unit)

The output unit 6 outputs the determination result that has been determined by the comparison unit 5. As the output unit 6 there are, for example, a display or printer, but is also possible to save the determination result by outputting to an appropriate storage device (not illustrated). In short, any device capable of notifying the determination result to medical staff or patient may be used as the output unit 6. The output unit 6 may also be configured to display the coefficient itself instead of only the determination result.

(Operation of this Embodiment)

Next, operation of the dementia differentiation device of this embodiment will be described with further reference to the flowchart shown in FIG. 3.

Figure 3:
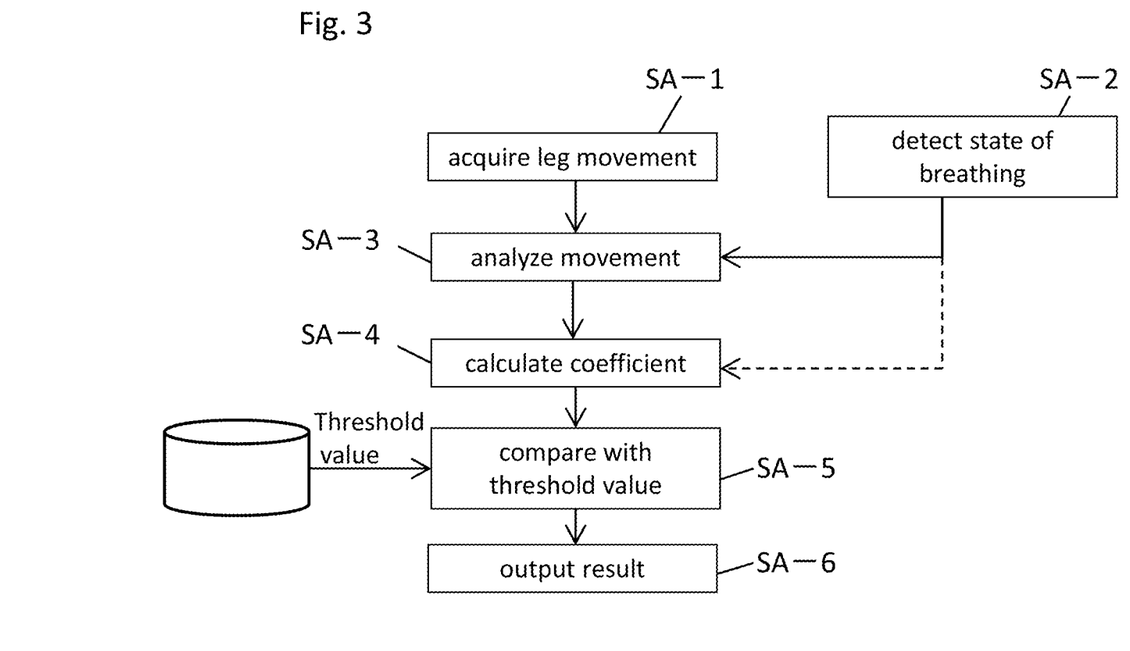
FIG. 3 is a flowchart for explaining a dementia differentiation procedure used in the device of FIG. 1.

(Step SA-1 in FIG. 3)

Figure 2:
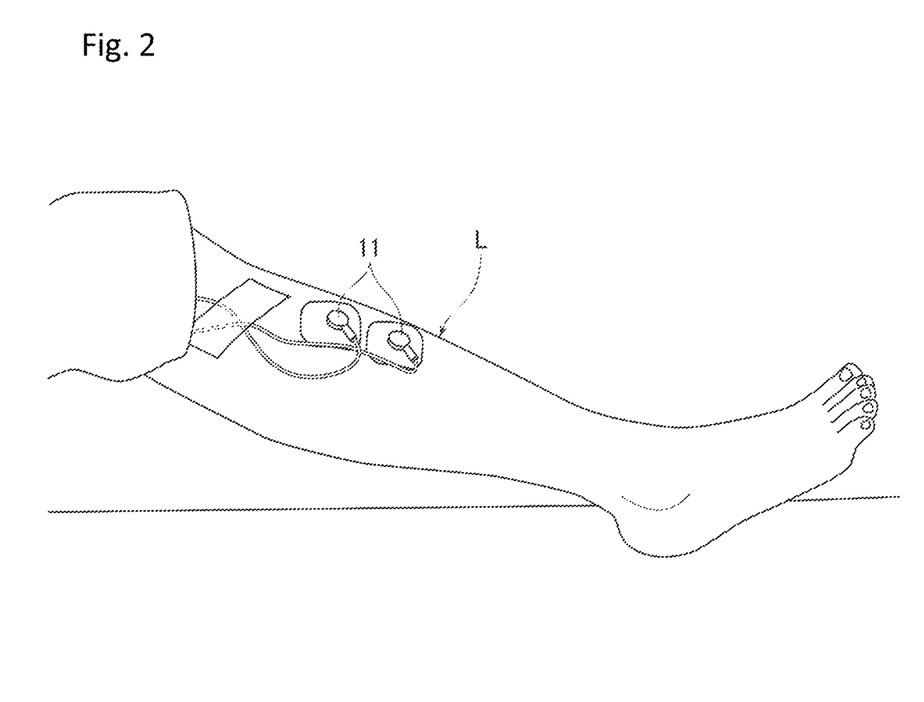
FIG. 2 is an explanatory drawing showing a state where electrodes for myoelectric detection are attached to a subject.
Figure 4:
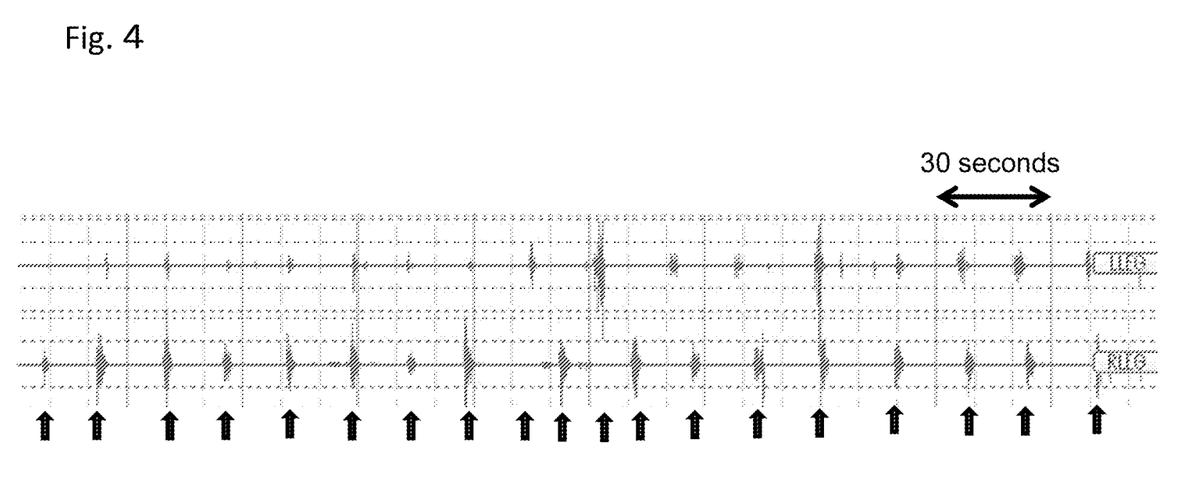
FIG. 4 is a specific example of a myoelectric diagram for a leg.

First, electrodes 11 of the leg movement acquisition unit 1 are attached to both the left and right legs of a subject (refer to FIG. 2). In this way it is possible to acquire leg movement of a sleeping subject. One example of a myoelectric diagram that has been acquired is shown in FIG. 4. In FIG. 4 the symbol LLEG indicates a myoelectric diagram for the left leg, and the symbol RLEG indicates a myoelectric diagram for the right leg. Regarding whether or not the subject is in a state of sleep, it is possible to determine by registering the bedtime and awakening time of the subject on the day of measurement, or to determine by appropriately using other support devices. Even if data for leg movements of both legs is stored in a single channel, the dementia differentiation described above is possible. It is also possible to acquire a myoelectric diagram for a single leg, and not both, but since leg movement is not necessarily produced equally in both legs, it is preferable to acquire movement of both legs.

(Step SA-2 in FIG. 3)

On the other hand, in parallel with acquisition of leg movement, whether or not the subject is in a state of apnea is detected by the apnea detection unit 2, and a detection result (air flow amount for nose and mouth, for example) is sent to the movement analysis unit 3. Alternatively the apnea detection unit 2 may carry out determination as to whether or not there is apnea using a predetermined threshold value, and send only flag information indicating that determination result to the movement analysis unit 3.

(Step SA-3 in FIG. 3)

Next, the movement analysis unit 3 determines whether or not the detected leg movement for left or right leg satisfies predetermined conditions, referring to the predetermined conditions. As has already been described, the specified conditions include at least the following conditions (a) to (d):

(a) the duration of leg movement is within a previously determined range;

(b) intensity of leg movement is a previously determined value or greater;

(c) leg movements satisfying conditions (a) and (b) continue for a previously determined number of times within a previously determined duration; and (d) the leg movement is not movement from immediately before to immediately after an apnea state.

Specific examples for each condition will be described in the following.

(Condition (a))

The duration of leg movement is set to 0.5-10 second with this example. That is, leg movement lasting a duration of 0.5-10 seconds is a condition. An example of a myoelectric diagram that satisfies this condition is shown at the tip of each arrow in FIG. 4.

(Condition (b))

As intensity of leg movement, it is possible to make the fact that a myoelectric value has increased to, for example, 8 pV or more since the time of calibration (at rest) a condition. However, in order to ensure detection of leg movement it is possible to consider appropriately changing this numerical value. There is also a possibility that the myoelectric value will increase due to any kind of noise. In this case, in order to appropriately determine leg movement it is preferable to provide means for removing the effects of noise. Alternatively, since a device is simplified by omitting such means, it is also possible to make the fact that swing in a myoelectric diagram from the time of calibration has increased to a specified value or more (for example, 25%) a condition.

(Condition (c))

Leg movements that satisfy the previously described conditions (a) and (b) continuing four times (specifically a predetermined number of times) or more with a movement interval of 5-90 seconds (specifically a predetermined time) is made a condition.

(Condition (d)) In the case where each of the above conditions is satisfied also, leg movement when apnea has been determined is not counted in the number of times of movement. Whether or not there is apnea may be determined based on detection result from the apnea detection unit 2. Apnea in this specification includes a so-called state of hypopnea. It is known that involuntary leg movement occurs in the case of recovering from a state of apnea, and by adding condition (d) it is possible to carry out differentiation of dementia accurately. In this condition, "immediately before" and "immediately after" can respectively be 0.5 seconds before and 0.5 seconds after, for example, but this numerical value can be appropriately changed in order to exclude the effects of apnea.

(Step SA-4 in FIG. 3)

Next, the coefficient calculation unit 4 counts a number of times of leg movement that have satisfied the above described predetermined conditions and calculates a coefficient based on this number of times. Specifically, as has been described above, PLM index (also called PLMs index) is used as the coefficient. In this case, the number of times of leg movement satisfying the above described conditions is called the PLM number of times. PLM index can be calculated from the following equation.

PLM index=PLM number of times/sleeping duration

Specifically, an average value for PLM number of times that have occurred per unit time may be used as the PLM index.

(Step SA-5 in FIG. 3)

Next, the comparison unit 5 determines a determination result for dementia differentiation by comparing a threshold value for determining whether or not the symptom is lewy body dementia with the coefficient (with this example, PLM index) that has been calculated by the coefficient calculation unit 4. With this example, the threshold value is stored in a suitable storage means. With this example, as the threshold value it is possible to use, for example, PLM coefficient >15.0, but the threshold value may be determined in accordance with required sensitivity or specificity.

Figure 5:
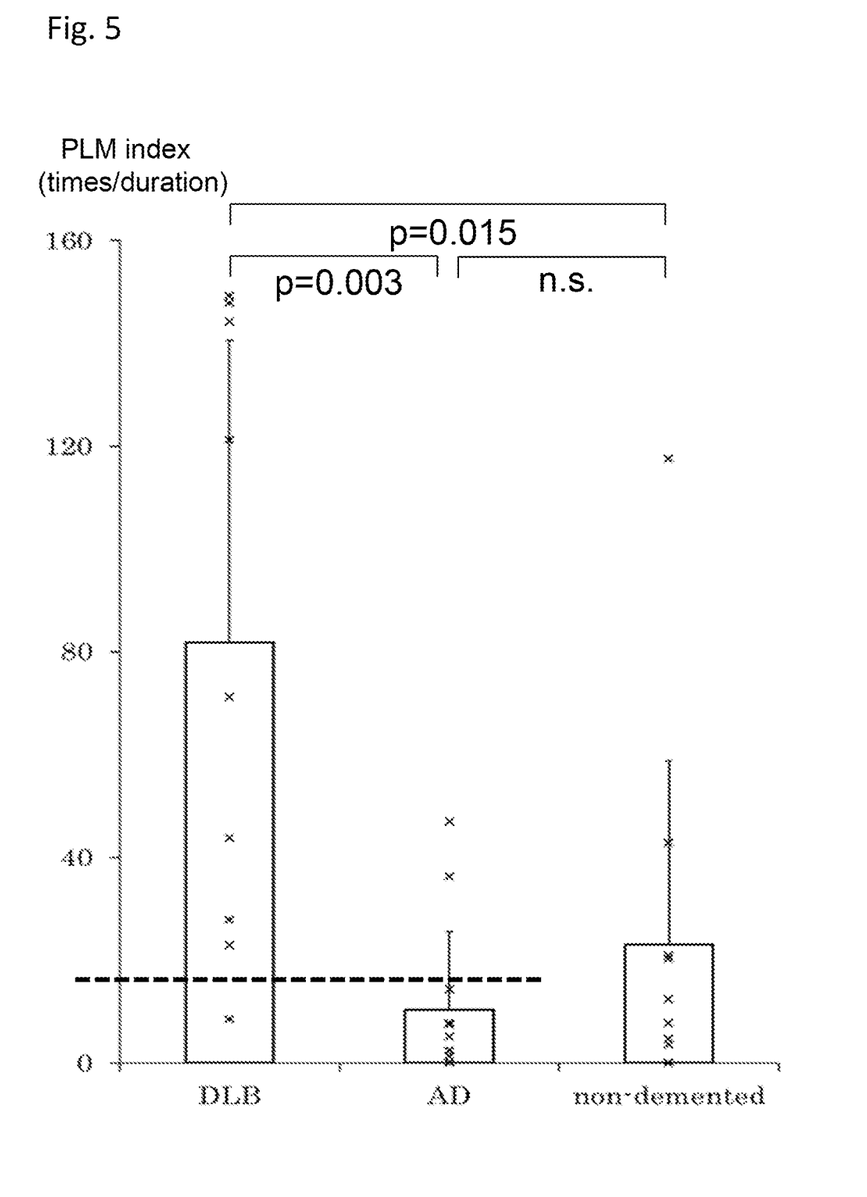
FIG. 5 is a graph showing PLM index actually acquired, with the vertical axis representing PLM index of each subject, and the horizontal axis representing a DLB group, an AD group and a control group.

A specific example of PLM index calculation results is shown in FIG. 5. DLB in the drawing is PLM index for a DLB patient group. Each "X" represents a value for an individual patient. Similarly, AD in the drawings represents PLM index of an AD patient group and "non-demented" represents PLM index of a control group. To which group a subject belongs was determined using separate diagnosis. Also, the control group did not suffer from DLB or AD, or any other type of dementia.

With the example of FIG. 5, it is possible to obtain a sensitivity of 88.9% and a specificity of 83.3% by making PLM index=15.0 a cutoff value (namely, PLM index >15.0). In this way it is possible to carry out differentiation of AD and DLB with a practically sufficient degree of accuracy. By making PLM index=8.0 a cutoff value, it is possible to obtain a sensitivity of 100.0% and a specificity of 75.0%. Also, reference symbol p in FIG. 5 represents a statistically-significant difference, with P<0.05 being statistically significant. As will be understood from FIG. 5, for the DLB group PLM value is clearly larger than for the AD group.

(Step SA-6 in FIG. 3)

Next, the output unit 6 outputs a determination result based on coefficient. In this way it is possible for authorized parties such as medical personnel to carry out differentiation as to whether dementia is AD or DLB. Operation of each of the above-described sections can be executed by a computer and a computer program installed in the computer.

The descriptions of the above-described embodiments and practical example are merely examples, and do not show the essential structure of the present invention. The structure of each part is not limited to the above description as long as it falls within the scope of the invention.

For example, each of the above-described structural elements can exist as a functional block, and may or may not exist as independent hardware. Also, as a method of implementation, it is possible to use hardware or to use computer software. Further, a single functional element of the present invention may be realized as a set of a plurality of functional elements, and a plurality of functional elements of the present invention may be implemented by a single functional element.

It is also possible for functional elements to be arranged at physically separate positions. In this case, it is also possible to connect functional elements using a network. It is possible to implement functions, or configure some of the functional elements, using grid computing or cloud computing.

Also, in the above-described embodiment, differentiation of dementia has been carried out by comparing a threshold value and a calculated coefficient (PLM value) in the comparison section, but the comparison section may be omitted. In this case, the output section outputs the calculated coefficient itself, and medical personnel can carry out differentiation of dementia based on this coefficient.

The invention claimed is:

1. A dementia differentiation device, comprising a leg movement acquisition unit, an apnea detection unit, a movement analysis unit a coefficient calculation unit and an output unit, wherein the leg movement acquisition unit continuously acquires leg movements of a sleeping subject, the apnea detection unit detects whether or not the subject is in a state of apnea, and the movement analysis unit determines whether or not the leg movements satisfy previously determined conditions, the previously determined conditions including at least the following conditions (a) to (d):

(a) the duration of leg movement is within a previously determined range;

(b) the intensity of leg movement is a previously determined value or greater;

(c) leg movements satisfying conditions (a) and (b) continue a previously determined number of times within a previously determined duration; and (d) the leg movement is not movement from immediately before until immediately after a state of apnea that has been detected by the apnea detection unit, and wherein the coefficient calculation unit calculates a coefficient based on the number of times of leg movement that satisfied the previously determined conditions, and the output unit outputs either the coefficient or a determination result based on the coefficient.

2. The dementia differentiation device of claim 1, further comprising a comparison unit, wherein the comparison unit determines the determination result by comparing a threshold value for determining whether or not a symptom is lewy body dementia and the coefficient that has been calculated by the coefficient calculation unit, and the output unit outputs the determination result that has been determined by the comparison unit.

3. The dementia differentiation device of claim 1, wherein the coefficient based on the number of times of leg movement is an average number of times per unit duration of the leg movement that satisfied the previously determined conditions, for the sleeping subject.

4. The dementia differentiation device of claim 1, wherein the leg movement acquisition unit acquires the leg movement by measuring myoelectric potential of a leg of the subject.

5. A computer program, for operation of a dementia differentiation device comprising a leg movement acquisition unit, an apnea detection unit, a movement analysis unit, a coefficient calculation unit and an output unit, wherein leg movement of a sleeping subject that has been acquired by the leg movement acquisition unit, and a detection result as to whether or not the subject is in a state of apnea, that has been detected by the apnea detection unit, are used, and the computer causes the movement analysis unit to execute a step of determining whether or not the leg movements satisfy previously determined conditions, the previously determined conditions including at least the following conditions (a) to (d):

(a) the duration of leg movement is within a previously determined range;

(b) the intensity of leg movement is a previously determined value or greater;

(c) leg movements satisfying conditions (a) and (b) continue a previously determined number of times within a previously determined duration; and (d) the leg movement is not movement from immediately before until immediately after a state of apnea that has been detected by the apnea detection unit, and wherein this computer program further causing a computer to execute a step of causing the coefficient calculation unit to calculate a coefficient based on the number of times of leg movement that satisfied the previously determined conditions, and a step of causing the output unit to output of either the coefficient or a determination result based on the coefficient.

6. An operating method for a dementia differentiation device, wherein leg movement of a sleeping subject and a detection result as to whether or not the subject is in a state of apnea are used, and a step of the movement analysis unit of the dementia differentiation device determining whether or not the leg movements satisfy previously determined conditions is provided, the previously determined conditions including at least the following conditions (a) to (d):

(a) the duration of leg movement is within a previously determined range;

(b) the intensity of leg movement is a previously determined value or greater;

(c) leg movements satisfying conditions (a) and (b) continue a previously determined number of times within a previously determined duration; and (d) the leg movement is not movement from immediately before until immediately after a state of apnea of the subject, and wherein the method further comprises a step of the coefficient calculation unit of the dementia differentiation device calculating a coefficient based on the number of times of leg movement that satisfied the previously determined conditions, and a step of the output unit of the dementia differentiation device outputting either the coefficient or a determination result based on the coefficient.

* * * * *